United States Patent [19]

Ogawa et al.

[11] Patent Number: 5,663,205
[45] Date of Patent: Sep. 2, 1997

[54] PHARMACEUTICAL COMPOSITION FOR USE IN GLAUCOMA TREATMENT

[75] Inventors: Takahiro Ogawa, Nishinomiya; Takaaki Deguchi, Kobe; Yoshifumi Ikejiri, Ibaraki; Katsuhiro Inada, Osaka, all of Japan

[73] Assignee: Senju Pharmaceutical Co. Ltd., Osaka, Japan

[21] Appl. No.: 338,592

[22] PCT Filed: May 19, 1993

[86] PCT No.: PCT/JP93/00654

§ 371 Date: Nov. 15, 1994

§ 102(e) Date: Nov. 15, 1994

[87] PCT Pub. No.: WO93/24121

PCT Pub. Date: Dec. 9, 1993

[30] Foreign Application Priority Data

May 22, 1992 [JP] Japan ................. 4-130828

[51] Int. Cl.$^6$ ................. A61K 31/18
[52] U.S. Cl. ................. 514/603; 514/601; 514/602; 514/913
[58] Field of Search ................. 514/601, 602, 514/603, 913

[56] References Cited

U.S. PATENT DOCUMENTS

| | | | |
|---|---|---|---|
| 4,127,674 | 11/1978 | Leopold | 424/324 |
| 4,217,305 | 8/1980 | Imai et al. | 260/556 |
| 4,816,604 | 3/1989 | Louis et al. | 564/349 |

FOREIGN PATENT DOCUMENTS

| | | |
|---|---|---|
| 0 375 560 | 6/1990 | European Pat. Off. |
| 0 382 629 A1 | 8/1990 | European Pat. Off. |
| WO 94/01096 | 1/1994 | WIPO |

OTHER PUBLICATIONS

Supplementary European Search Report for Application No. 93910356 dated Dec. 21, 1994.
Database WPI, Derwent Publications Ltd., London, GB; Application No. 66–25519F, 1966.
Database WPI, Derwent Publications Ltd., London, GB; Application No. 89–047015, 1989.
Database WPI, Derwent Publications Ltd., London, GB; Application No. 82–18211E, 1982.
Drugs Future, vol. 19, No. 7, Jul. 1994, p. 683, "Amosulalol Hydrochloride Lowgan".

*Primary Examiner*—Zohreh Fay
*Attorney, Agent, or Firm*—Merchant, Gould, Smith, Edell, Welter & Schmidt, P.A.

[57] ABSTRACT

A pharmaceutical composition for use in glaucoma treatment which contains as an active ingredient 5-[1-hydroxy-2-[2-(2-methoxyphenoxyl)ethylamino]ethyl]-2-methylbenzenesulfonamide of the formula:

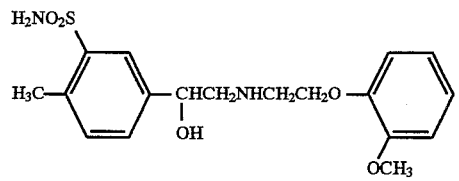

or its acid salt. This agent is free from side effects and stable and has an excellent intraocular pressure reducing activity at its low concentrations, thus being useful as a pharmaceutical composition for use in glaucoma treatment.

12 Claims, 4 Drawing Sheets

PHARMACEUTICAL COMPOSITION FOR USE IN GLAUCOMA TREATMENT

This invention relates to a pharmaceutical composition for use in glaucoma treatment that is virtually free from side effects, stable, and can develop improved intraocular pressure reducing activity at low concentrations.

Glaucoma is a disease characterized by an abnormal increase in intraocular pressure which provokes a variety of symptoms, such as fatigability in the eye, blurred vision, pain in the eye and gradually impaired vision, eventually leading to the risk of loss of vision. The disease causes the eyeball to harden like stone or the depth of the pupil to look green.

Inside the eyeball a watery fluid (the aqueous humor) circulates invariably to maintain a constant pressure within the eye (intraocular pressure=15 to 20 mmHg). The aqueous humor is controlled by the circulation of blood or lymph, resilience of the eyeball wall, action of the dominant nerve etc., and when any of such factors becomes abnormal, intraocular pressure rises and glaucoma develops.

When such abnormality is caused by ophthalmic diseases such as iritis, wounds and hemorrhage in the vitreous body, the resultant disease is called secondary glaucoma. However, the usual type of glaucoma is primary glaucoma in which the abnormality is brought about by unknown causes.

Primary glaucoma is classified into three types: (1) inflammatory glaucoma whose progress is acute, (2) simple glaucoma whose progress is chronic and (3) congenital glaucoma.

In order to treat glaucoma, heretofore, various medicaments have been used with the specific aim of preventing a rise in intraocular pressure or reducing increased intraocular pressure. The intraocular pressure reducing agents known so far include the sympathomimetic drugs such as epinephrine, but epinephrine, with its mydriatic activity prompts angle closure when applied to narrow angle glaucoma, thus possibly causing a rapid increase in intraocular pressure and often producing an increase in blood pressure and pigmentation in the conjunctiva.

The parasympathomimetic drugs such as pilocarpine, with their miotic activity, bring about the sensation of darkness or accommodation abnormality in the visual field.

In recent years, furthermore, β-adrenergic blocking agents such as timolol, by virtue of their suppressory effect against production of aqueous humor, have been extensively used for the treatment of glaucoma (Drug Therapy Practical Series, The Drug Treatment of Glaucoma, pp. 70 to 75, 1990). Nevertheless, such β-adrenergic blocking agents, which have been reported to cause systemic side effects such as bradycardia, cardiac insufficiency and asthma onset, cannot be administered to patients with such symptoms.

It is indicated that $\alpha_1$-adrenergic blocking agents promote an aqueous humor outflow, and bunazosin hydrochloride can increase choroidal blood flow, leading to the suggestion that a possibility could be opened up for the development of a novel therapeutic agent against low tension glaucoma (Journal of Japanese Society of Ophthalmology, vol. 42, pp. 710 to 714, 1991). So, this drug substance is considered to find application in the treatment of glaucoma, but conjunctival hyperemia and miosis owing to its vasodilatory activity would be inevitable.

In contrast to the above, β-adrenergic stimulants also are expected to be given to such patients but conventional β-adrenergic stimulants such as salbutamol fail to demonstrate satisfactory activity unless applied at high concentrations, which consequently brings about marked conjunctival hyperemia, thus rendering its continued administration impossible.

As described above, in fact, there has so far not been found satisfactory glaucoma treatment agents that are free from the above-mentioned side effects and remain stable and effective at low concentrations.

In recent years, it was reported that phenylethanolamine derivatives or their salts, inclusive of 5-[1-hydroxy-2-[2-(2-methoxyphenoxy) ethylamino]ethyl]-2-methylbenzenesulfonamide hydrochloride (hereinafter referred to as amosulalol hydrochloride), exhibit both α-adrenergic and β-adrenergic blocking activities and are effective as hypertensive agents and treatment agents for angina pectoris (Japanese-Unexamined Patent Publication No. 95544/1979).

The above-described compounds showing both α-adrenergic and β-adrenergic blocking activities were reported to improve the disadvantage of side effects caused by the combined application of α-adrenergic and β-adrenergic blocking agents and thus to be effective as α, β-blocking agents, specifically as active ingredients for antihypertensives, agents for treatment of angina pectoris antiarrhythmic agents, etc. (Japanese Unexamined Patent Publication No. 73610/1980).

In view of such circumstances, the present inventors repeatedly conducted intensive research to find a drug substance that is free entirely from the defects (side effects) pertaining to the conventional medicaments mentioned above and exhibits the combined mechanisms of action to suppress aqueous humor formation and promote aqueous humor outflow to thereby develop effective intraocular pressure reducing activity at low concentrations. As a result, the present inventors found that amosulalol hydrochloride as described in the above Japanese Patent Publication can surprisingly exhibit unexpected excellent intraocular pressure reducing activity and produce fewer of the side effects observed with the conventional drugs, while it is stable and effective at low concentrations, and have completed this invention.

The present invention has as an object to provide a pharmaceutical composition for use in glaucoma treatment that is free from the above defects (side effects), stable, and possessing effective intraocular pressure reducing activity at low concentrations.

Namely, this invention relates to a novel and useful pharmaceutical composition for use in glaucoma treatment which contains as an active ingredient 5-[1-hydroxy-2-[2-(2-methoxyphenoxy)ethylamino]ethyl]-2-methylbenzenesulfonamide (hereinafter referred to as "amosulalol") represented by the formula:

or its acid salt. The acid salt includes, for example, salts with inorganic acids such as hydrochloride and sulfate, and salts with organic acids such as maleate, tartrate and citrate, with the hydrochloride (i.e. amosulalol hydrochloride) being preferred.

Amosulalol or its hydrochloride, that constitutes the active agent for the glaucoma treatment agent of this invention, is described, in terms of physiochemical properties and production process, for example in the above-mentioned Japanese Unexamined Patent Publication No. 95544/1979.

The glaucoma treatment composition according to this invention, as may be evident from the test examples given below, exhibits improved intraocular pressure reducing activity at low concentrations, while it shows lessened toxicity and remains stable. Consequently, the glaucoma treatment composition can be used as an effective drug in the treatment of various types of glaucoma.

In utilizing amosulalol or its hydrochloride as a pharmaceutical composition for use in glaucoma treatment, such active ingredient can be mixed with per se known pharmacologically allowable carriers, excipients, diluents, etc., and processed into preparations for parenteral application such as ophthalmic solutions, ophthalmic ointments and injectable solutions and preparations for oral administration such as tablets, capsules and granules.

In cases where the glaucoma treatment composition of this invention is used in the form of an ophthalmic solution for example, buffers, tonicity agents, preservatives, auxiliary solubilizers (stabilizers), pH regulating agents, thickening agents, chelating agents and other additives which are conventionally formulated into ophthalmic solutions can suitably be added, as far as they would not affect adversely the objective of this invention.

Among the above additives, the buffer includes, for example, phosphate buffers, borate buffers, citrate buffers tartrate buffers, acetate buffers and amino acids.

As the tonicity agent, there may be mentioned, for example, sugars such as sorbitol, glucose and mannitol polyhydric alcohols such as glycerol, polyethylene glycol and propylene glycol, and salts such as sodium chloride.

Examples of the preservative include benzalkonium chloride, benzethonium chloride, p-hydroxybenzoic acid esters such as methyl and ethyl hydroxybenzoates, benzyl alcohol, phenethyl alcohol, sorbic acid or its salts, thimerosal and chlorobutanol.

As the auxiliary solubilizer, there may be mentioned, for example, cyclodextrins and their derivatives, water-soluble polymers such as polyvinylpyrrolidone, surfactants, etc., with polyvinylpyrrolidone and cyclodextrin preferably being used.

The pH regulating agent includes, for example, hydrochloric acid, acetic acid, phosphoric acid, sodium hydroxide, ammonium hydroxide and potassium hydroxide.

Examples of the thickening agent include hydroxyethylcellulose, hydroxypropylcellulose, methylcellulose, hydroxypropylmethylcellulose, carboxymethylcellulose and their salts.

As the chelating agent, there may be mentioned, for example, sodium edeate, sodium citrate and condensed sodium phosphates.

In cases where the pharmaceutical composition for use in glaucoma treatment of this invention is utilized as an ophthalmic ointment, purified lanolin, petrolatum, plastibase, liquid paraffin, polyethylene glycol, etc. are suitably employed as an ophthalmic ointment base.

Furthermore, the glaucoma treatment composition of this invention can be used in the form of preparations for oral administration such as tablets, capsules and granules, as well as in the form of injectable solutions.

The glaucomas treatment composition of this invention is administered in varying doses depending upon the route of administration, symptoms, age and body weight of a patient etc. and, when used in the form of an ophthalmic solution for adults, for example, is desirably applied as an ophthalmic solution containing the active agent of amosulalol or its salt at concentrations in the range of about 0.001 to 5.0 w/v %, preferably in the range of about 0.05 to 1.0 w/v %, once to four times a day in one. to several drops each.

In cases where the glaucoma treatment composition of this invention is used in the form of an ophthalmic ointment, it is desirable to apply an ophthalmic ointment having a content of the active agent in the range of about 0.001 to 10 w/w %, preferably in the range of 0.05 to 1.0 w/w %, once to four times a day according to the severity of the symptoms.

The glaucoma treatment composition of this invention can suitably be admixed with one or not less than two of other glaucoma treatment compositions, unless it is contrary to the objective of this invention.

The glaucoma treatment composition of this invention can suitably be incorporated with other ingredients having different efficacies in addition to the glaucoma treatment composition, unless it is contrary to the objective of this invention.

Another aspect of the present invention is a pharmaceutical composition for use in glaucoma treatment comprising amosulalol hydrochloride and polyvinylpyrrolidone or α-cyclodextrin. Amosulalol hydrochloride in the form of a solution is stable toward heat and light, but when cooled, the solution freezes and even after return to room temperature, crystals formed while freezing do not easily dissolve. Therefore, it has been a problem to use the solution after preserving in a cool place.

The present inventors, seeking a pharmaceutical composition which has no such a defect, found that by adding polyvinylpyrrolidone or α-cyclodextrin to a solution of amosulalol the solution can be used without leaving crystals.

In this aspect of the invention too, the above-mentioned buffers, tonicity agents, preservatives, auxiliary solubilizers (stabilizers), pH regulating agents, thickening agents, chelating agents and other additives which are conventionally formulated into ophthalmic solutions can suitably be added as far as they would not affect adversely the objective of this invention.

Described in the below are examples and test examples to illustrate this invention in more detail and to clarify the effects of this invention, but these are given as mere illustrations and are not to be understood to limit the scope of this invention.

EXAMPLES

Example 1

Ophthalmic Solution

An ophthalmic solution was prepared in accordance with the following formulation:

| | |
|---|---|
| Amosulalol hydrochloride | 0.05 g |
| Mannitol | 5.0 g |
| Sodium dihydrogenphosphate | 0.1 g |
| Methyl p-hydroxybenzoate | 0.02 g |
| Propyl p-hydroxybenzoate | 0.01 g |
| Dilute hydrochloric acid | In appropriate amount (pH 6.0) |

The above ingredients were admixed with sterile purified water to make up to 100 ml in total.

Example 2

Ophthalmic Solution

An ophthalmic solution was prepared in accordance with the following formulation:

| | |
|---|---|
| Amosulalol hydrochloride | 0.1 g |
| Boric acid | 2.0 g |
| Benzalkonium chloride | 0.005 g |
| Sodium hydroxide | In appropriate amount (pH 6.0) |

The above ingredients were admixed with sterile purified water to make up to 100 ml in total.

Example 3

Ophthalmic Solution

An ophthalmic solution was prepared in accordance with the following formulation:

| | |
|---|---|
| Amosulalol hydrochloride | 0.25 g |
| Conc. glycerol | 2.6 g |
| Sodium acetate | 0.1 g |
| α-Cyclodextrin | 0.1 g |
| Methyl p-hydroxybenzoate | 0.02 g |
| Propyl p-hydroxybenzoate | 0.01 g |
| Dilute hydrochloric acid | In appropriate amount (pH 4.5) |

The above ingredients were admixed with sterile purified water to make up to 100 ml in total.

Example 4

Ophthalmic Solution

An ophthalmic solution was prepared in accordance with the following formulation:

| | |
|---|---|
| Amosulalol hydrochloride | 0.5 g |
| Conc. glycerol | 2.6 g |
| Sodium acetate | 0.1 g |
| Benzalkonium chloride | 0.005 g |
| Dilute hydrochloric acid | In appropriate amount (pH 5.5) |

The above ingredients were admixed with sterile purified water to make up to 100 ml in total.

Example 5

Ophthalmic Solution

An ophthalmic solution was prepared in accordance with the following formulation:

| | |
|---|---|
| Amosulalol hydrochloride | 0.5 g |
| Conc. glycerol | 2.6 g |
| Sodium acetate | 0.1 g |
| Polyvinylpyrrolidone | 0.5 g |
| Benzalkonium chloride | 0.005 g |
| Dilute hydrochloric acid | In appropriate amount (pH 5.0) |

The above ingredients were admixed with sterile purified water to make up to 100 ml in total.

Example 6

Ophthalmic Solution

An ophthalmic solution was prepared in accordance with the following formulation:

| | |
|---|---|
| Amosulalol hydrochloride | 1.0 g |
| Conc. glycerol | 2.6 g |
| Sodium monohydrogenphosphate | 0.1 g |
| Polyvinylpyrrolidone | 1.0 g |
| Sodium edeate | 0.05 g |
| Benzalkonium chloride | 0.005 g |
| Sodium hydroxide | In appropriate amount (pH 4.0) |

The above ingredients were admixed with sterile purified water to make up to 100 ml in total.

Example 7

Ophthalmic Ointment

An ophthalmic ointment was prepared in accordance with the following formulation:

| | |
|---|---|
| Amosulalol hydrochloride | 1.0 g |
| Liquid paraffin | 1.0 g |
| White petrolatum | In appropriate amount |
| Total amount | 100 g |

Example 8

Ophthalmic Ointment

An ophthalmic ointment was prepared in accordance with the following formulation:

| | |
|---|---|
| Amosulalol hydrochloride | 0.5 g |
| Liquid paraffin | 1.0 g |
| White petrolatum | In appropriate amount |
| Total amount | 100 g |

TEST EXAMPLES

Test Example 1

Intraocular Pressure Reducing Activity of Amosulalol Hydrochloride on Normal Intraocular Pressure in Pigmented Rabbits Male pigmented rabbits (Dutch belted rabbits) weighing about 2 kg, after having been confirmed to be free from ocular abnormalities; were bred in a breeding room maintained at a temperature of 24± 4° C. and at a relative humidity of 55± 15%, while they were given solid food (Labo RG-RO manufactured by Nihon Nohsan Kogyo K.K.) at a daily rate of 100 g per rabbit and allowed free access to tap water as drinking water.

As a test drug, amosulalol hydrochloride was processed into 0.05% (hereinafter, the term "%" is to be understood to designate "w/v %") and 1.0% aqueous solutions which were used in the test, and 0.5% timolol maleate ophthalmic solution [Timoptol (registered trademark): Ban-yu Pharmaceutical Co.] and physiological saline were used as a positive control drug and a control substance, respectively.

(1) Measurement of intraocular pressure:

Thirty two (32) rabbits were divided into four groups each consisting of 8 rabbits, and 50 µl of test drugs as well as the control drug and physiological saline were applied topically to one eye each of the individual rabbits, with the other being left untreated. Before instillation and 0.5, 1, 2, 3, 4, 6 and 8 hours after topical application, intraocular pressure for both of eyes of each rabbit was measured using a Pneumatonograph (manufactured by Alcon Co. Hereinafter referred to briefly as "PTG").

Figure 1:
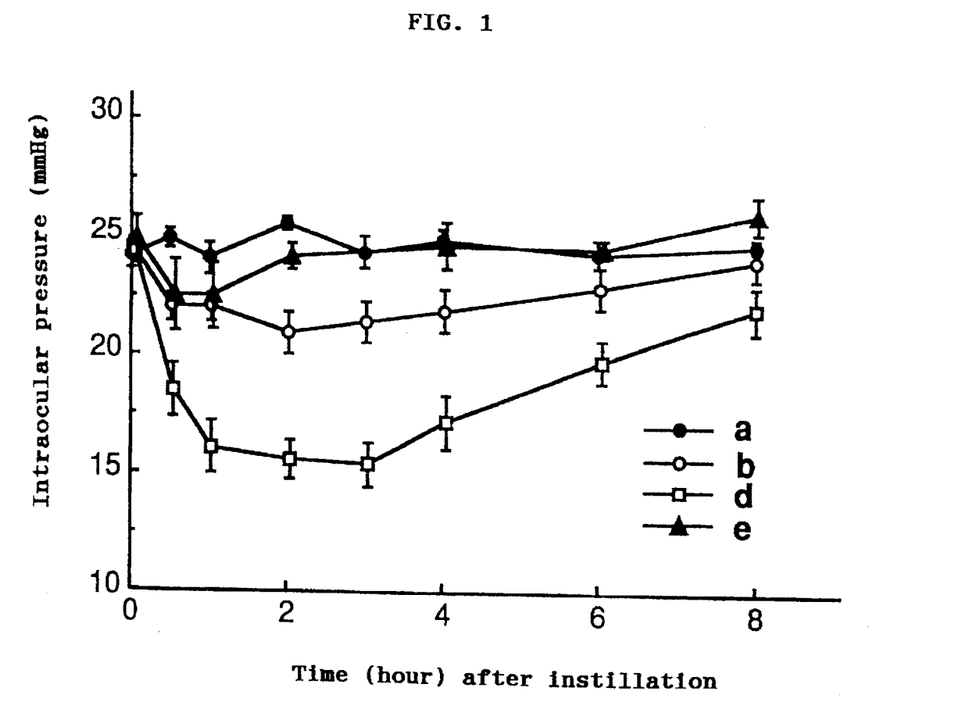
FIG. 1 shows intraocular pressure after time of instillation.

Shown in FIG. 1 are time-course changes of intraocular pressure taken with the eyes treated by instillation of each of the test drugs, control drug and physiological saline, with time (hour) after instillation taken as abscissa and intraocular pressure (mmHg as ordinate; each value in mean±S.E. (number of cases is 8). The signs "a", "b", "d" and "e" designate physiological saline, 0.05% aqueous solution of amosulalol hydrochloride, 1.0% aqueous solution of amosulalol hydrochloride, and 0.5% ophthalmic solution of timolol maleate, respectively.

As is evident from the results shown in FIG. 1, topical application of 1.0% aqueous solution of amosulalol hydrochloride showed a marked decrease in intraocular pressure being sustained from 30 min after instillation to 6 hours, wherein the maximum decrease in intraocular pressure of 9.0 mmHg was found 3 hours after instillation. 0.05% aqueous solution of amosulalol hydrochloride attained a maximum decrease in intraocular pressure 2 hours after topical application corresponding to 3.6 mmHg.

Instillation of 0.5 % timolol maleate ophthalmic solution used as a positive control drug realized only a slight drop in intraocular pressure as low as 2.4 mmHg 30 min and 1 hour after topical application.

(2) Measurement of pupil diameter:

With each of the rabbits as used under the above item (1), pupil diameter was measured for both eyes using a micrometer caliper, before instillation and 0.5, 1, 2, 3, 4, and 6 hours after topical application of the individual test drugs and physiological saline, respectively. The pupil diameter measurements taken with the eyes treated with each of the test drugs showed a variance within the normal range, with no significant change in the pupil diameter being found in both groups. This may lead to confirmation that amosulalol hydrochloride did not exert any effect on the pupil diameter.

Test Example 2

Intraocular Pressure Reducing Activity of Amosulalol Hydrochloride on Normal Intraocular Pressure in Pigmented Rabbits Forty (40) male pigmented rabbits (Dutch belted rabbits) weighing about 2 kg, after having been confirmed to be free from ocular abnormalities, were bred in a breeding room maintained at a temperature of 24± 4° C. and at a relative humidity of 55± 15%, while they were fed solid food (Labo RG-RO, manufactured by Nihon Nohsan Kogyo K.K.) at a daily rate of 100 g per rabbit and allowed free access to tap water as drinking water.

As a test drug, amosulalol hydrochloride was processed into 0.05%, 0.5% and 1.0% aqueous solutions which were used in the test, and 0.5% timolol maleate ophthalmic solution [Timoptol (registered trademark): Ban-yu Pharmaceutical Co.] and physiological saline were used as a positive control drug and a control substance, respectively.

(1) Measurement of intraocular pressure:

Forty (40) rabbits were divided into five groups. each consisting of 8 heads, and 50 µl of test drug as well as the control drug and physiological saline were applied topically to one eye each of the individual rabbits, with the other being left untreated. Before instillation and 0.5, 1, 2, 3, 4, 6 and 8 hours after topical application respectively, intraocular pressure for both eyes of each rabbit was measured using PTG.

Figure 2:
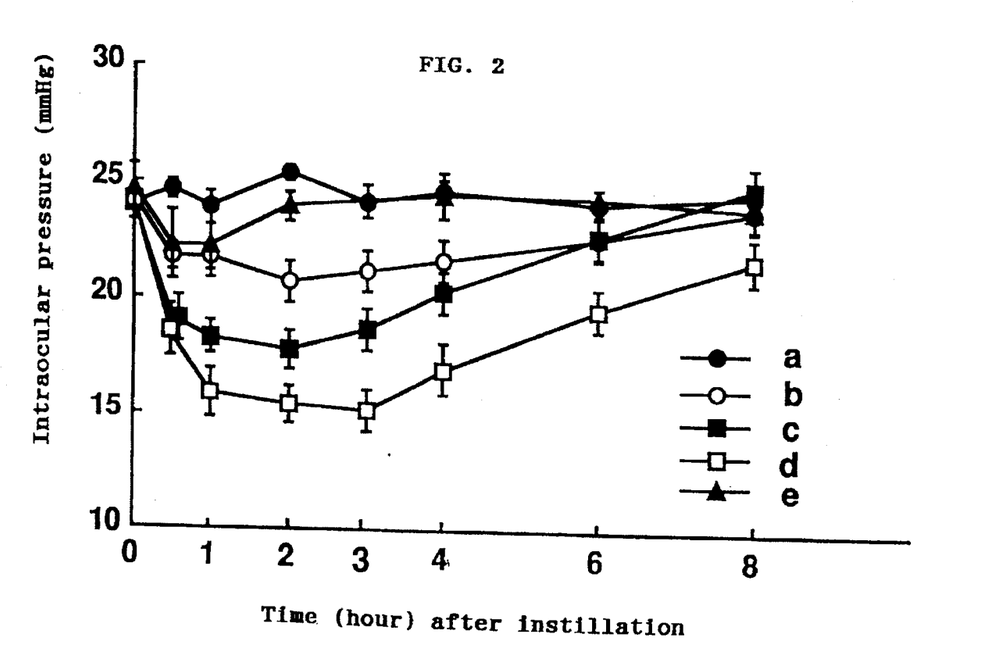
FIG. 2 shows intraocular pressure after time of instillation.
Figure 3:
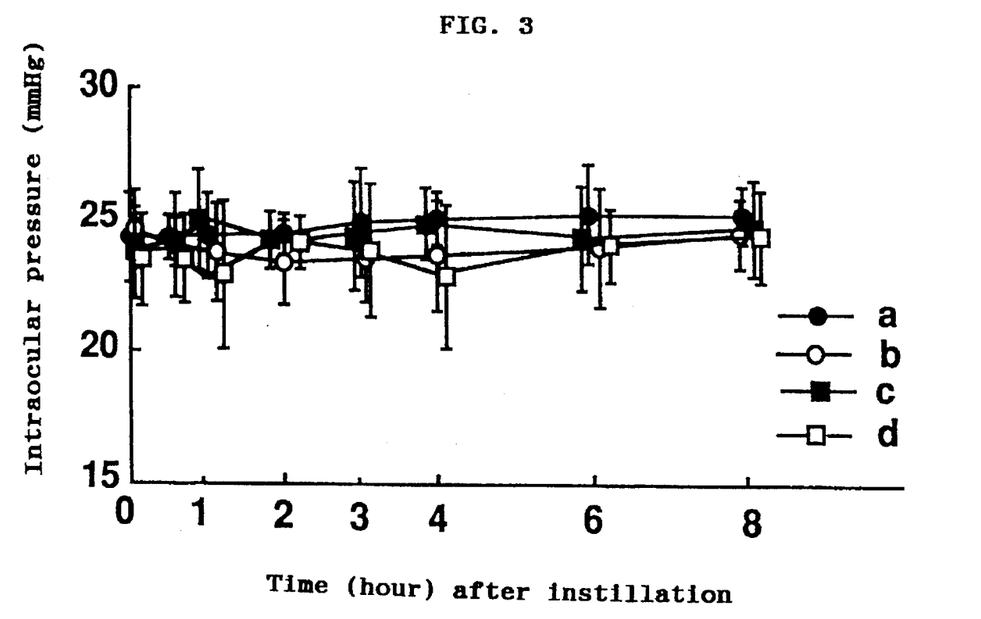
FIG. 3 shows intraocular pressure after time of instillation.

Time-course changes of intraocular pressure measurements taken with the eyes treated by instillation of each of the test drugs, control drug and physiological saline, are illustrated in FIGS. 2 (for treated eyes) and 3 (for non-treated eyes), respectively, with time (hour) after instillation taken as abscissa and intraocular pressure (mmHg) as ordinate; each value in mean ± S.E. (the number in each case is 8). The signs "a", "b", "c", "d" and "e" designate physiological saline, 0.05% aqueous solution of amosulalol hydrochloride, 0.5% aqueous solution of amosulalol hydrochloride, 1.0% aqueous solution of amosulalol hydrochloride and 0.5% solution of timolol maleate, respectively.

As is evident from the results shown in FIG. 2 (for treated eyes), topical application of 1.0% aqueous solution of amosulalol hydrochloride showed a marked decrease in intraocular pressure being sustained from 30 min after instillation to 6 hours, wherein the maximum decrease in intraocular pressure of 9.0 mmHg was found to take place 3 hours after instillation. 0.5% aqueous solution of amosulalol hydrochloride realized a significant drop in intraocular pressure from 30 min to 4 hours after topical application, and the maximum decrease in intraocular pressure of 6.2 mmHg was developed 2 hours after topical application. 0.05% aqueous solution of amosulalol hydrochloride exhibited a maximum drop in intraocular pressure 2 hours after instillation which corresponded to 3.6 mmHg.

Instillation of 0.5% timolol maleate ophthalmic solution used as a positive control drug realized only a slight drop in intraocular pressure as low as 2.4 mmHg 30 min and 1 hour after topical application, respectively.

As is apparent from the results shown in FIG. 3 (for non-treated eyes), no significant change was noticed in intraocular pressure for the other eyes in the groups treated with the respective test drugs, which may lead to confirmation that amosulalol hydrochloride does in no way affect the other non-treated eyes.

(2) Measurement of pupil diameter:

With each of the rabbits as used under the above item (1), pupil diameter was measured for both eyes using a micrometer caliper, before instillation and 0.5, 1, 2, 3, 4, and 6 hours after topical application of the respective test drugs and physiological saline, respectively.

Figure 4:
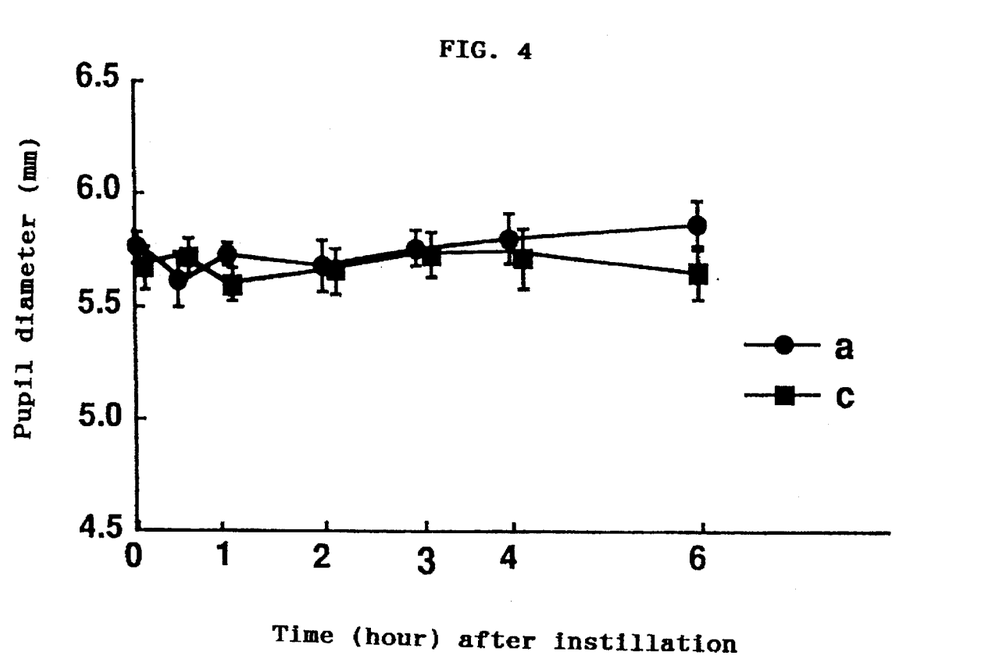
FIG. 4 shows pupil diameter after time of instillation.

FIG. 4 shows time-course changes of pupil diameter taken with the eyes treated with each of the test drugs, with time (hour) after instillation taken as abscissa and pupil diameter (mm) as ordinate; each value in mean ± S.E. (a number of the cases is 8). The signs "a" and "c" designate physiological saline, 0.5% aqueous solution of amosulalol hydrochloride, respectively.

As is evident from the results illustrated in FIG. 4, the pupil diameter measurements in the groups treated with each of the test drugs showed a variance within the normal range, with no significant change in the pupil diameter being noticed in both groups. This may lead to confirmation that amosulalol hydrochloride did not exert any effect on the pupil diameter.

The above results have indicated that amosulalol hydrochloride exhibited significant intraocular pressure reducing activity toward normal eyes in pigmented rabbits and, at low concentrations as small as 0.05%, developed more potent intraocular pressure reducing activity than 0.5% timolol maleate ophthalmic solution. It was also proven that amosulalol hydrochloride, which did not affect the pupil diameter and at concentrations of less than 0.5%, produced merely a slight degree of conjunctival hyperemia, would be a clinically safe medicament.

Test Example 3

Intraocular Pressure Reducing Activity of Amosulalol Hydrochloride by Consecutive Application for 5 Days on Normal Intraocular Pressure in Pigmented Rabbits Eight (8) male pigmented rabbits weighing about 2 kg, after having been confirmed to be free from ocular abnormalities, were bred in a breeding room maintained at a temperature of 24±4° C. and at a relative humidity of 55±15%, while they were given solid food (Labo RG-RO, manufactured by Nihon Nohsan Kogyo K.K.) at a daily rate of 100 g per rabbit and allowed free access to tap water as drinking water.

For the 8 pigmented rabbits bred by the above procedure, 50 µl of 0.5% aqueous solution of amosulalol hydrochloride was applied to one eye, with 50 µl of physiological saline being given topically to the other. Intraocular pressure was measured before the first instillation and at regular intervals of 1 hour up to 8 hours after application on Days 1 and 5, and before the first instillation and 2 or 3 hours after application on Days 2, 3 and 4, respectively, with intraocular pressure additionally being measured 24 hours after the first instillation on Day 5.

Figure 5:
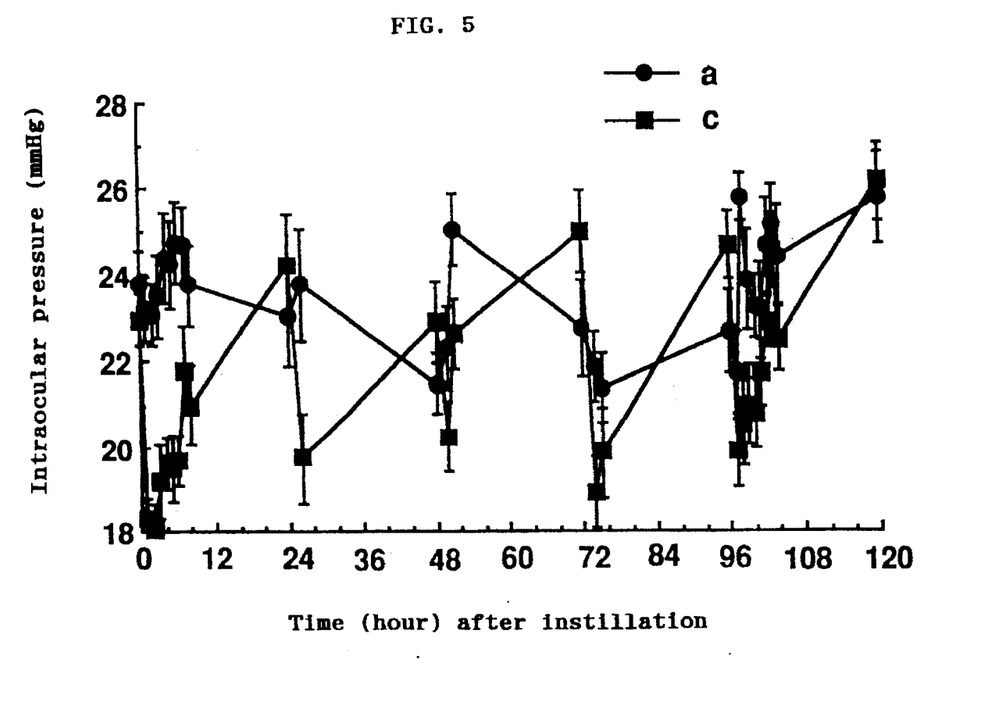
FIG. 5 shows intraocular pressure after time of instillation.

FIG. 5 shows time-course changes over the 5 day period in intraocular pressure caused by consecutive instillation of 0.5% aqueous solution of amosulalol hydrochloride three times a day, with time (hour) after instillation taken as abscissa and intraocular pressure (mmHg) as ordinate; each value in mean ± S.E. (number of cases is 8). The signs "a" and "c" designate physiological saline, 0.5% aqueous solution of amosulalol hydrochloride, respectively.

As is evident from the results shown in FIG. 5, the maximum drop in intraocular pressure of 4.8 mmHg was noticed 2 hours after the first instillation on Day 1; the second instillation done 4 hours later was not found to bring about any further decrease in intraocular pressure, but produced significant intraocular pressure drop, with the intraocular pressure being found to return to the initial value 24 hours later. On Day 2, significant decrease in intraocular pressure was observed 2 hours after instillation as was the case with Day 1, whereas no significant intraocular pressure drop was caused on Day 3. However, significant decrease in intraocular pressure was also noted on Day 4, and at any measuring time on Day 5, there was observed almost the same degree of intraocular pressure decrease as on Day 1.

The above results have demonstrated that 0.5% aqueous solution of amosulalol hydrochloride, when applied consecutively to the eyes of pigmented domestic rabbits three times a day for 5 days, produced almost the same degree of intraocular pressure decrease on any treated days, thus leading to confirmation that amosulalol hydrochloride is free from tachyphylaxis.

Test Example 4

Intraocular Pressure Reducing Activity of 0.5% Aqueous Solution of Amosulalol Hydrochloride on Hypertensive Itraocular Pressure Induced by Water Loading White Rabbits With 5 male white rabbits weighing about 2 kg used as test animals, 50 µl of 0.5% aqueous solution of amosulalol hydrochloride was applied to one eye of each rabbit, with 50 µl of physiological saline being given to the other, and drinking water, 60 ml/kg (37° C.) was loaded by means of an oral probe 30 min later. Intraocular pressure was measured for both eyes using PTG before instillation as well as before water loading and 0.5, 1, 2 and 4 hours after the same.

Figure 6:
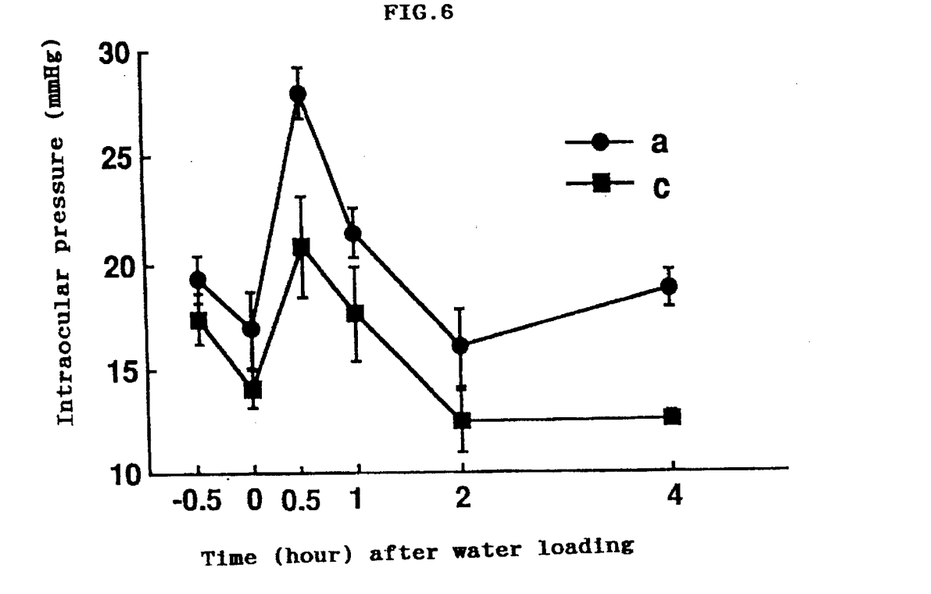
FIG. 6 shows intraocular pressure after time of water loading.

FIG. 6 is a graph showing the intraocular pressure reducing activity of 0.5% aqueous solution of amosulalol hydrochloride on hypertensive intraocular pressure induced by water loading in white rabbits with time (hour) after instillation taken as abscissa and intraocular pressure (mmHg) as ordinate; each value in mean ± S.E. (number of cases is 8).

As may be apparent from the results shown in FIG. 6, the intraocular pressure in physiological saline increased by 8.7 mmHg 30 min after water loading, and it returned to the initial level 2 hours later. In contrast to this, 0.5% aqueous solution of amosulalol hydrochloride increased in intraocular pressure by 3.4 mmHg 30 min after water loading, resulting in the finding that 0.5% aqueous solution of amosulalol hydrochloride significantly reduced the increase in intraocular pressure, as compared with physiological saline.

Test Example 5

Intraocular Pressure Reducing Activity of 0.5% Aqueous Solution of Amosulalol Hydrochloride on Hypertensive Intraocular Pressure Induced by Laser Irradiation in Pigmented Rabbits With 5 male pigmented rabbits weighing about 2 kg used as test animals, 50 µl of 0.5% aqueous solution of amosulalol hydrochloride was applied in a 50 µl portion to one eye of each rabbit, with 50 µl of physiological saline being given to the other. 30 min later, a laser beam was irradiated onto 6 different spots (spot size: 200 μm, power of 0.5 W, for 0.1 sec) of the irises in both eyes in such a manner that the spots were located at an equal distance. Intraocular pressure was measured for both eyes using PTG before instillation as well as before laser irradiation and 15, 30 and 45 min after laser irradiation.

Figure 7:
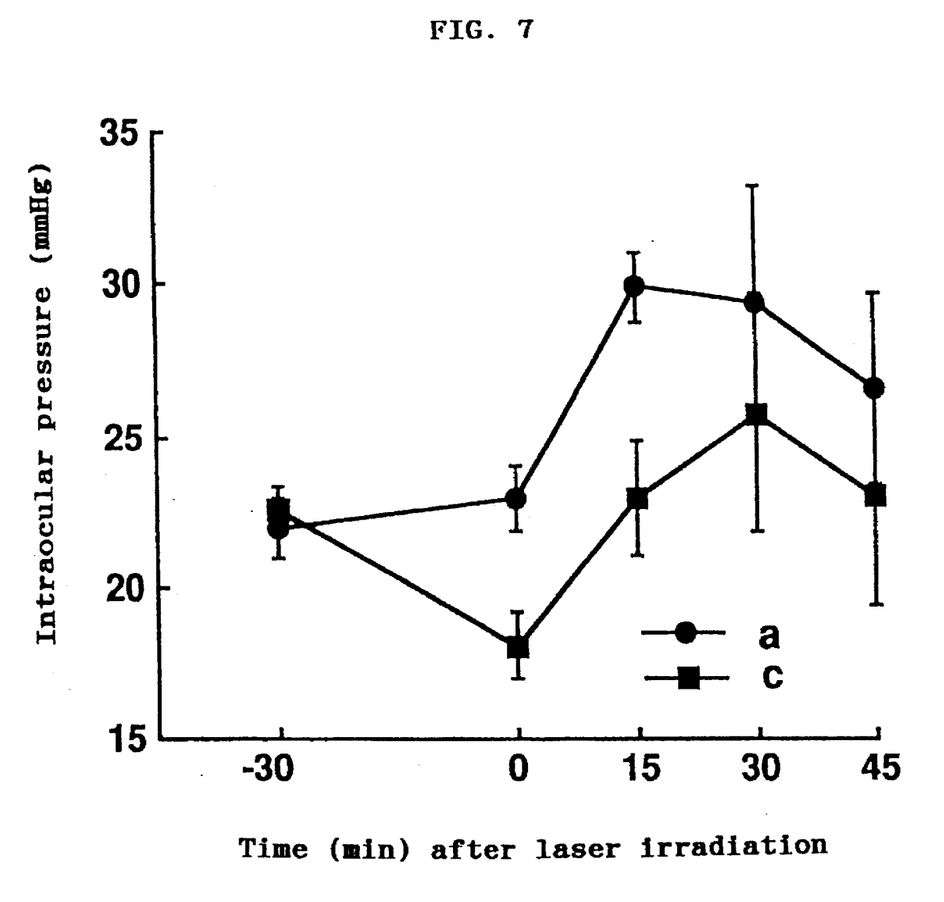
FIG. 7 shows intraocular pressure after time of laser irradiation.

FIG. 7 is a graph showing the intraocular pressure reducing activity of 0.5% aqueous solution of amosulalol hydrochloride on hypertensive intraocular pressure induced by laser irradiation in pigmented rabbits, with time (min) after laser irradiation taken as abscissa and intraocular pressure (mmHg) as ordinate; each value in mean ± S.E. (the number in each case is 8). The signs "a" and "c" designate physiological saline and 0.5% aqueous solution of amosulalol hydrochloride, respectively.

As is apparent from the results shown in FIG. 7, intraocular pressure in physiological saline group increased by 7.9 mmHg about 15 min after laser irradiation, and it returned to the initial level 45 min later, whereas 0.5% aqueous solution of amosulalol hydrochloride decreased intraocular pressure by 4.5 mmHg 30 min after instillation (i.e immediately before laser irradiation) but increased to almost the same level as before instillation, leading to the finding that 0.5% aqueous solution of amosulalol hydrochloride exhibits suppressory activity against increase of the intraocular pressure.

The above results demonstrate that amosulalol not only exhibits marked intraocular pressure reducing activity toward normal intraocular pressure in rabbits but also develops outstanding suppressory activity against raised intraocular pressure in rabbits as induced by water loading or by laser irradiation.

Test Example 6

Investigation on the Processing of Amosulalol Hydrochloride into Ophthalmic Solution: Freeze-Thaw Test (Investigation on a Stabilizing Agent for the Ophthalmic Solution of Amosulalol Hydrochloride)

Amosulalol hydrochloride, as processed in an aqueous solution, was found to remain stable against heat and light. When 0.5% aqueous solution of amosulalol hydrochloride (pH 5.5) was subjected to a freeze-thaw test, however, the once frozen solution did not allow the crystals to dissolve even after being left on standing at room temperature.

Consequently, investigation was conducted on a stabilizing agent intended for use in the case of such freezing.

0.5% aqueous solution of amosulalol hydrochloride (pH 5.5), after being admixed with each of the stabilizing agents (Nos. 1 to 5) as described in Table 1 shown below, was filled into a glass ampoule of 5 ml capacity, frozen at −30° C. and left standing at room temperature to conduct inspection for the presence of crystals in it.

TABLE 1

| No. | Stabilizing agent |
|-----|-------------------|
| 1 | Hydroxypropylmethylcellulose SH-50 |
| 2 | Polyvinylpyrrolidone K-30 |
| 3 | Polysorbate 80 |
| 4 | α-Cyclodextrin |
| 5 | β-Cyclodextrin |

The obtained results are shown in Table 2. As is evident from the results shown in Table 2, polyvinylpyrrolidone K-30 (Stabilizing agent No. 2) and α-cyclodextrin (Stabilizing agent No. 4) were found to be effective. Consequently, it was found advisable to use polyvinylpyrrolidone or α-cyclodextrin as a stabilizing agent for amosulalol hydrochloride.

TABLE 2

| Stabilizing agent | Precipitation of crystals Freeze-thaw test |
|-------------------|--------------------------------------------|
| Not added | + |
| No. 1 | + |
| No. 2 | − |
| No. 3 | + |
| No. 4 | − |
| No. 5 | + |

Note: In Table 2 as shown above, the sign "+" designates "precipitation of crystals" and "−" means "No precipitation of crystals".

Test Example 7

Toxicity Test of Amosulalol Hydrochloride (1) Acute toxicity test of amosulalol hydrochloride with mice:

Investigation was conducted on the acute toxicity of amosulalol hydrochloride in mice through oral administration or intravenous administration.

Amosulalol was given to 7-weeks aged ICR mice by oral administration by use of an oral probe or through a tail vein. As a result, the values of 50% lethal dose ($LD_{50}$) were determined to be 6500 mg/kg (male) and 5700 mg/kg (female), when administered orally, and 104 mg/kg (male) and 134 mg/kg (female), when administered intravenously.

(2) Ocular local toxicity test in rabbits of 1.0% and 0.5% ophthalmic solutions of amosulalol hydrochloride by consecutive instillation for 28 days:

With 15 male Japanese white rabbits divided into 3 groups each consisting of 5 rabbits, 1.0% and 0.5% ophthalmic solutions of amosulalol hydrochloride as well as physiological saline as a control were applied in one drop (0.05 ml) per time to the right eye of each rabbit alone, four times a day at a regular interval of 2.5 hours, for 28 days consecutively with the left eye being left untreated.

Observation was done on the following items of (a) to (f):

(a) General conditions; Observation was made on the mice for general conditions once a week.

(b) Body weight measurement; Body weight was measured once a week.

(c) Visual observation on the anterior ocular segment; Based on the below-described criteria for assessment of ocular injuries (*Gendai no Rinsho* (Present-Day Clinics) Vol. 4, No. 4, pp. 227–289, 1970), numerical rating was performed on 1.0% and 0.5% ophthalmic solutions of amosulalol hydrochloride before instillation as well as on the day (Day 1) of initiating the instillation and on the 2nd, 4th, 7th, 14th, 21st, 28th days after initiating the instillation but each time after completion of the instillation and on the morning of the last instillation (29th day). With reference to the results of numerical rating, a numerical rating of not less than 1 as determined on either of the items was understood to be judged "injurious to the eye" while numerical ratings of 0 and 0.5 were considered "not injurious to the eye".

Criteria for assessment of ocular injuries:

Cornea

A) Degree of Opacity

| | |
|---|---|
| No opacity (Normal) | 0 |
| Scattered or diffuse areas, details of iris clearly visible) | 1 |
| Easily discernible translucent areas details of the iris slightly obscured | 2 |
| Opalescent areas, no details of iris visible, size of pupil barely discernible | 3 |
| Opaque, iris invisible | 4 |

B) Area of opacity

| | |
|---|---|
| One quarter (or less) but not 0 | 1 |
| Greater than one quarter but less than half | 2 |
| Greater than half but less than three quarters | 3 |
| Greater than three quarters, up to whole area | 4 |

Iris

Value:

| | |
|---|---|
| Normal | 0 |
| Folds above normal, congestion, swelling circumcorneal hyperemia (any of all of these or any combination), iris reacts to light (sluggish reaction is positive) | 1 |
| No reaction to light, hemorrhage, gross destruction (any or all of these) | 2 |

Conjunctiva

A) Redness of palpebral conjunctiva

| | |
|---|---|
| No hyperemia | 0 |
| Mucosa tinged very slightly with red, a slight vasodilation in the palpebral edge | 0.5 |
| Obvious hyperemia above normal, mucosa tinged more definitely with red, prominent swelling | 1 |
| Mucosa tinged very markedly with red, slightly indistinct peripheral vessels | 2 |
| Diffuse beefy red (more severe than 2) | 3 |

B) Edema of palpebral conjunctiva

| | |
|---|---|
| No swelling | 0 |
| Slight edematous tendency | 0.5 |
| Swelling above normal | 1 |
| Obvious swelling with partial eversion of lids | 2 |
| Swelling with lids about half closed | 3 |
| Swelling with lids about half closed to completely closed | 4 |

C) Redness of bulbar conjunctiva

| | |
|---|---|
| No hyperemia | 0 |
| Slight dilation of circumcorneal vessels | 0.5 |
| More prominent vasodilation | 1 |
| Marked dilation of vessels coursing toward the palpebral edge of the vessels tinged markedly red | 2 |

D) Nictitating membrane

| | |
|---|---|
| No hyperemia | 0 |
| Tendency toward vasodilation and edema | 0.5 |
| More prominent vasodilation, the palpebral edge tinged with red | 1 |
| Very marked vasodilation, the whole nictitating membrane tinged with red | 2 |

E) Discharge

| | |
|---|---|
| No discharge | 0 |
| Any amount different from normal (does not include small amounts observed in inner canthus) | 1 |
| Discharge with moistening of the lids and hair just adjacent to lids | 2 |
| Discharge with moistening of the lids and hair, and considerable area around the eye | 3 |

Tables 5 and 6 show the results of the visual observation on the anterior ocular section, being specified above under Item (c), as obtained with 1.0% and 0.5% ophthalmic solutions of amosulalol hydrochloride, respectively, wherein each value given represents a mean for 5 cases.

In Tables 5 and 6, the numerical rating of cornea means the value obtained by multiplying a value in "(A) Degree of Opacity" by that of "(B) Area of opacity" in the above-described "Criteria for assessment of ocular injuries".

TABLE 5

| Item of Assessment | Time elapsed after appl'n. of 1.0% sol'n., days | | | | | | | |
|---|---|---|---|---|---|---|---|---|
| | Before | 1 | 2 | 4 | 7 | 14 | 21 | 28 | 29 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva | | | | | | | | | |
| (A) | 0 | 0.2 | 0.2 | 0.1 | 0.1 | 0.1 | 0.1 | 0.1 | 0 |
| (B) | 0 | 0 | 0 | 0 | 0 | 0 | 0 | 0 | 0 |
| (C) | 0 | 0.5 | 0.5 | 0.5 | 0.3 | 0.3 | 0.3 | 0.3 | 0 |
| (D) | 0 | 0 | 0 | 0 | 0 | 0 | 0 | 0 | 0 |
| (E) | 0 | 0 | 0 | 0 | 0 | 0 | 0 | 0 | 0 |
| Total | 0 | 0.7 | 0.7 | 0.6 | 0.4 | 0.4 | 0.4 | 0.4 | 0 |

TABLE 6

| Item of Assessment | Time elapsed after appl'n. of 0.5% sol'n., days | | | | | | | |
|---|---|---|---|---|---|---|---|---|
| | Before | 1 | 2 | 4 | 7 | 14 | 21 | 28 | 29 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva | | | | | | | | | |
| (A) | 0 | 0 | 0 | 0 | 0 | 0 | 0 | 0 | 0 |
| (B) | 0 | 0 | 0 | 0 | 0 | 0 | 0 | 0 | 0 |
| (C) | 0 | 0.4 | 0.4 | 0.2 | 0.2 | 0.2 | 0.1 | 0.1 | 0 |
| (D) | 0 | 0 | 0 | 0 | 0 | 0 | 0 | 0 | 0 |
| (E) | 0 | 0 | 0 | 0 | 0 | 0 | 0 | 0 | 0 |
| Total | 0 | 0.4 | 0.4 | 0.2 | 0.2 | 0.2 | 0.1 | 0.1 | 0 |

(d) Observation on fluorescein-dyed spots of the cornea:

Before instillation of 1.0% and 0.5% ophthalmic solutions of amosulalol hydrochloride as well as on the day (Day 1) of initiating the instillation and on the 2nd, 4th, 7th, 14th, 21st, 28th days after initiating the instillation but each time after completion of such instillation, and on the morning of the last instillation (29th day), 10 µl of 0.1% aqueous fluorescein solution was applied topically to the eyes of each test animal, and observation was performed on the abrasion of the corneal epithelial cells with a photo-slit lamp.

(e) Evaluation with a scanning electron microscope of corneal epithelial and endothelial cells;

After completion of the instillation of 1.0% and 0.5% ophthalmic solutions of amosulalol hydrochloride, morphological observation was done on corneal epithelial and endothelial cells in 3 eyes each of the two groups.

(f) Evaluation with an optical microscope of a sagittal section of the eyeball;

After completion of the instillation of 1.0% and 0.5% ophthalmic solutions of amosulalol hydrochloride, specimens for optical microscopy were prepared each having a sagittal section of the eyeball from 2 eyes each of the two groups to conduct microscopic examination of the eyelid, conjunctiva, cornea, anterior segment, iris, crystalline lens vitreous body, retinochoroid membrane, screla and optic nerve. As a result, no abnormalities in (a) general conditions and (b) body weight measurement were observed with both 1% and 0.5% ophthalmic solutions of amosulalol hydrochloride; (c) visual observation of the anterior ocular segment revealed no abnormality in both of the groups treated individually with 1.0% and 0.5% ophthalmic solutions of amosulalol hydrochloride, as is shown in Tables 5 and 6; and furthermore, (d) observation of fluorescein-dyed spots in the cornea, (e) evaluation with a scanning electron microscope of corneal epithelial and endothelial cells and (f) evaluation with an optical microscope of a sagittal section of the eyeball individually disclosed no abnormalities with either of 1% and 0.5% ophthalmic solutions of amosulalol hydrochloride.

The above-described results of the different tests have led us to the finding that amosulalol hydrochloride, when used as an ophthalmic solution for the treatment of glaucoma, is free from side effects such as ocular irritation and can offer an extremely safe medicament.

The glaucoma treatment agent of this invention, at its low concentrations, exhibits excellent intraocular pressure reducing activity and is low in toxicity and safe, thus finding advantageous application as a treatment agent against various types of glaucoma.

We claim:

1. A method of treating glaucoma, comprising administering to a human subject in need thereof an effective amount in treating glaucoma of 5-[1-hydroxy-2-[2-(2-methoxyphenoxy)ethylamino]ethyl]-2-methylbenzenesulfonamide of the formula:

or its acid salt.

2. The method of claim 1, wherein the 5-[1-hydroxy-2-[2-(2-methoxyphenoxy)ethylamino]ethyl]-2-methylbenzenesulfonamide is administered in the form of a pharmaceutical composition further comprising a pharmaceutically acceptable carrier.

3. The method of claim 2, wherein the carrier is an ophthalmic carrier.

4. The method of claim 3, wherein the composition is an ophthalmic solution.

5. The method of claim 3, wherein the composition is an ophthalmic ointment.

6. The method of claim 2, wherein the carrier comprises polyvinylpyrrolidone or α-cyclodextrin.

7. A method of reducing intraocular pressure in a human subject in need thereof, comprising administering an amount effective in reducing intraocular pressure of 5-[1-hydroxy-2-[2-(2-methoxyphenoxy)ethylamino]ethyl]-2-methylbenzenesulfonamide of the formula:

or its acid salt.

8. The method of claim 7, wherein the 5-[1-hydroxy-2-[2-(2-methoxyphenoxy)ethylamino]ethyl]-2-methylbenzenesulfonamide is administered in the form of a pharmaceutical composition further comprising a pharmaceutically acceptable carrier.

9. The method of claim 8, wherein the carrier is an ophthalmic carrier.

10. The method of claim 9, wherein the composition is an ophthalmic solution.

11. The method of claim 9, wherein the composition is an ophthalmic ointment.

12. The method of claim 8, wherein the carrier comprises polyvinylpyrrolidone or α-cyclodextrin.

* * * * *

UNITED STATES PATENT AND TRADEMARK OFFICE
CERTIFICATE OF CORRECTION

PATENT NO. : 5,663,205

DATED : September 2, 1997

INVENTOR(S) : OGAWA ET AL.

It is certified that error appears in the above-identified patent and that said Letters Patent is hereby corrected as shown below:

On the title page, item
[73], Assignees should appear as:

Senju Pharmaceutical Co. Ltd, Osaka, Japan; and
Yamanouchi Pharmaceutical Co., Ltd., Tokyo, Japan Signed and Sealed this Third Day of March, 1998

Attest:

BRUCE LEHMAN

*Attesting Officer*  *Commissioner of Patents and Trademarks*